(12) United States Patent
Pierro

(10) Patent No.: US 11,992,302 B2
(45) Date of Patent: *May 28, 2024

(54) SYSTEM AND METHOD FOR NON-INVASIVELY DETERMINING AN INDICATION AND/OR AN ASSESSMENT OF INTRACRANIAL PRESSURE

(71) Applicant: Vivonics, Inc., Bedford, MA (US)

(72) Inventor: Michele Pierro, Westford, MA (US)

(73) Assignee: Vivonics, Inc., Bedford, MA (US)

( * ) Notice: Subject to any disclaimer, the term of this patent is extended or adjusted under 35 U.S.C. 154(b) by 196 days.

This patent is subject to a terminal disclaimer.

(21) Appl. No.: 17/396,015

(22) Filed: Aug. 6, 2021

(65) Prior Publication Data

US 2021/0361181 A1    Nov. 25, 2021

Related U.S. Application Data

(63) Continuation of application No. 17/139,092, filed on Dec. 31, 2020, now Pat. No. 11,109,771.

(Continued)

(51) Int. Cl.
| | | |
|---|---|---|
| *A61B 5/00* | (2006.01) | |
| *A61B 5/03* | (2006.01) | |
| *A61B 5/145* | (2006.01) | |

(52) U.S. Cl.
CPC ............ *A61B 5/031* (2013.01); *A61B 5/0059* (2013.01); *A61B 5/14542* (2013.01); *A61B 5/6814* (2013.01)

(58) Field of Classification Search
CPC ... A61B 5/031; A61B 5/0059; A61B 5/14542; A61B 5/6814; A61B 5/0075; A61B 5/14553
See application file for complete search history.

(56) References Cited

U.S. PATENT DOCUMENTS

| | | | |
|---|---|---|---|
| 4,204,547 | A | 5/1980 | Allocca |
| 5,074,310 | A | 12/1991 | Mick |

(Continued)

FOREIGN PATENT DOCUMENTS

| | | |
|---|---|---|
| CN | 109009064 A | 12/2018 |
| CN | 209450518 U | 10/2019 |

(Continued)

OTHER PUBLICATIONS

Written Opinion from the International Searching Authority for International Application No. PCT/US2020/067616, dated Mar. 30, 2021, eight (8) pages.

(Continued)

*Primary Examiner* — May A Abouelela
(74) *Attorney, Agent, or Firm* — Iandiorio Teska & Coleman, LLP

(57) ABSTRACT

A system for non-invasively determining an indication and/or an assessment of intracranial pressure (ICP) is featured. The system includes at least one intracranial light source adapted to be placed on skin above a cranium of a living subject configured to emit light which penetrates the cranium and targets intracranial space of a living subject. The system includes a least one extracranial light source adapted to be placed on skin above a predetermined area of the living subject configured to emit light which penetrates and targets extracranial space of the living subject. A detector subsystem including at least a first detector is configured to detect reflected light from the intracranial space and the extracranial space and is configured to output intracranial output signals associated with light detected from the intracranial space and/or output extracranial output signals associated with light detected from the extracranial space. A processing subsystem is coupled to the at least one intracranial light source, the at least one extracranial light source, and the (Continued)

detector subsystem. The processing subsystem is configured to determine intracranial oxygen saturation and extracranial oxygen saturation and non-invasively determine an indication and/or an assessment of ICP using a ratio of the intracranial oxygen saturation to the extracranial oxygen saturation.

2 Claims, 10 Drawing Sheets

Related U.S. Application Data

(60) Provisional application No. 62/956,725, filed on Jan. 3, 2020.

(56) References Cited

U.S. PATENT DOCUMENTS

| | | | |
|---|---|---|---|
| 5,596,987 A * | 1/1997 | Chance | G01N 21/49 600/476 |
| 6,117,089 A | 9/2000 | Sinha | |
| 6,390,989 B1 * | 5/2002 | Denninghoff | A61B 3/16 600/561 |
| 6,406,427 B1 * | 6/2002 | Williams | A61B 5/4076 600/301 |
| 6,589,189 B2 | 7/2003 | Meyerson et al. | |
| 7,104,958 B2 | 9/2006 | Crutchfield et al. | |
| 7,547,283 B2 | 6/2009 | Mourad et al. | |
| 7,559,898 B2 | 7/2009 | Eide | |
| 8,277,385 B2 | 10/2012 | Berka et al. | |
| 8,366,627 B2 | 2/2013 | Kashif et al. | |
| 8,512,260 B2 | 8/2013 | Grudic et al. | |
| 8,696,593 B2 | 4/2014 | Campbell et al. | |
| 9,138,181 B2 * | 9/2015 | Haisley | A61B 5/1455 |
| 9,737,246 B2 | 8/2017 | Kato | |
| 9,826,913 B2 | 11/2017 | Galea | |
| 9,895,070 B2 | 2/2018 | Galea | |
| 10,264,986 B2 | 4/2019 | Galea | |
| 10,285,630 B2 * | 5/2019 | Takagi | A61H 31/004 |
| 10,674,923 B2 | 6/2020 | Melker et al. | |
| 11,089,972 B2 | 8/2021 | Sutin et al. | |
| 11,109,771 B2 | 9/2021 | Pierro | |
| 2005/0187488 A1 * | 8/2005 | Wolf | A61B 5/031 128/903 |
| 2008/0077023 A1 * | 3/2008 | Campbell | A61B 5/031 600/502 |
| 2009/0143656 A1 | 6/2009 | Manwaring et al. | |
| 2009/0234245 A1 * | 9/2009 | Jaffe | A61B 5/0059 600/561 |
| 2009/0326345 A1 * | 12/2009 | Jaffe | A61B 5/6814 600/323 |
| 2010/0268096 A1 | 10/2010 | Berka et al. | |
| 2011/0201961 A1 * | 8/2011 | Hu | A61B 5/318 600/561 |
| 2011/0201962 A1 * | 8/2011 | Grudic | A61B 5/02405 600/561 |
| 2013/0150687 A1 | 6/2013 | Kato | |
| 2013/0245397 A1 | 9/2013 | Grudic et al. | |
| 2013/0289422 A1 | 10/2013 | Swoboda et al. | |
| 2014/0180046 A1 | 6/2014 | Campbell et al. | |
| 2016/0058395 A1 | 3/2016 | Muser et al. | |
| 2016/0128587 A1 * | 5/2016 | Kuenen | A61B 3/1241 600/561 |
| 2018/0070831 A1 * | 3/2018 | Sutin | A61B 5/031 |
| 2018/0103861 A1 * | 4/2018 | Sutin | A61B 5/029 |
| 2018/0110449 A1 | 4/2018 | Maeda et al. | |
| 2020/0069254 A1 * | 3/2020 | Lange | A61B 5/291 |
| 2020/0113461 A1 * | 4/2020 | Sanz Garcia | G16H 50/20 |

FOREIGN PATENT DOCUMENTS

| | | |
|---|---|---|
| CN | 110786843 A | 2/2020 |
| CN | 111528811 A | 8/2020 |
| CN | 212394901 U | 1/2021 |
| CN | 113440123 A | 9/2021 |
| CN | 215227603 U | 12/2021 |
| CN | 114795171 A | 7/2022 |
| EP | 3068294 A1 | 9/2016 |
| EP | 4061204 A1 | 9/2020 |
| JP | 2002010986 A | 1/2002 |
| WO | 1996025876 A1 | 8/1996 |
| WO | 2015073903 A1 | 5/2015 |
| WO | 2016164891 A1 | 10/2016 |
| WO | 2020069229 A1 | 4/2020 |
| WO | 2021099426 A1 | 5/2021 |

OTHER PUBLICATIONS

Franceschini et al., "Near-Infrared Spiroximetry: Noninvasive Measurements of Venous Saturation in Piglets and Human Subjects", Innovative Techniques, J. Appl. Physiol., (2002), 92 pp. 372-384.

Yanagisawa et al., Partial optical path length in the scalp in subject-specific head models for multi-distance probe configuration of near infrared spectroscopy, Proceedings of SPIE, (2018) Event: SPIE Structured Light, 2018, Yokohama, Japan, four (4) pages.

Franceschini et al., "Noninvasive Optical Method of Measuring Tissue and Arterial Saturation: An Application to Absolute Pulse Oximetry of the Brain", Optics Letters, Jun. 15, 1999, 24, No. 12, pp. 829-831.

Zhao et al., "Optical Hemoglobin Extinction Coefficient Data Set For Near-Infrared Spectroscopy", Biomedical Optics Express 5151, Nov. 1, 2017, 8, No. 11, nine (9) pages.

Mizuno et al., "A Functional NIRS Study of Brain Functional Networks Induced by Social Time Coordination", Brain Sciences, (2019) 9, 43, eleven (11) pages.

Olsson et al., "Regional cerebral saturation monitoring with near-infrared spectroscopy during selective antegrade cerebral perfusion: Diagnostic performance and relationship to postoperative stroke", Surgery for Acquired Cardiovascular Disease, The Journal of Thoracic and Cardiovascular Surgery, Feb. 2006, 131, No. 2, eleven (11) pages.

* cited by examiner

SYSTEM AND METHOD FOR NON-INVASIVELY DETERMINING AN INDICATION AND/OR AN ASSESSMENT OF INTRACRANIAL PRESSURE

RELATED APPLICATIONS

This application is a continuation of U.S. patent application Ser. No. 17/139,092 filed Dec. 31, 2020 and claims benefit of and priority to U.S. Provisional Application Ser. No. 62/956,725 filed Jan. 3, 2020, under 35 U.S.C. §§ 19, 120, 363, 365, and 37 C.F.R. § 1.55 and § 1.78, which is incorporated herein by this reference.

GOVERNMENT RIGHTS

This invention was made with U.S. Government support under Contract No. W81XWH-17-C-0006, awarded by the U.S. Army. The Government has certain rights in the invention.

FIELD OF THE INVENTION

This invention relates to a system and method for non-invasively determining an indication and/or an assessment of intracranial pressure (ICP).

BACKGROUND OF THE INVENTION

Traumatic Brain Injury (TBI) is a complex and heterogeneous disorder that may result in a large spectrum of associated injury severity. The brain is a soft organ with delicate structures held within a fixed volume. Damage to the small structures within a brain may cause local swelling (ICP) and cerebral blood flow and systemic blood pressure may not necessarily decrease with brain swelling. This elevated ICP may cause more damage which may lead to a negative spiral that may result in dire health sequelae which may include brain cell death and permanent brain injury or death. In many active populations a person with a brain injury may try to ignore the seemingly mild symptoms of headache, dizziness and the like. However, an unknown percentage of such injured persons may be experiencing clinically significant elevated ICP which may worsen or lead to permanent brain damage. Early detection of elevated ICP could reduce the risks associated with undiagnosed ICP and provide for timely medical care including, inter alia, pharmacological or surgical interventions.

One conventional system and method to non-invasively monitor ICP relies on optical coupling with source probes and detectors and diffuse correlation spectroscopy. See e.g., WO 2016/164891, incorporated by reference herein. Another conventional system for non-invasive assessment of hemodynamic functional state of the brain teaches using near-infrared spectroscopy (NIRs) to transmit light through a body part which is measured by a light sensor. See e.g., U.S. Publ. No. 2010/0268096, incorporated by reference herein. The '096 patent application teaches an optical measurement block which carries information about the blood flow through the brain and the value of intracranial pressure. Another known system for an oxygen saturation measuring sensor and oxygen saturation measuring apparatus teaches a plurality of light sources and a plurality of light receiving elements that detect the near-infrared light having wavelengths corresponding to oxyhemoglobin and deoxyhemoglobin to calculate oxygen saturation. See e.g., U.S. Publ. No. 2018/0110449, incorporated by reference herein. Non-invasively determining intracranial oxygen saturation and extracranial oxygen saturation is also known. See e.g., Yanagisuwa et al., *Partial Optical Path Length in the Scalp in Subject-Specific Head Models For Multi-Distance Probe Configuration of Near Infrared Spectroscopy*, Proceedings Volume 10711, Biomedical imaging and Sensing Conference, (2018), incorporated by reference herein.

However, to date there appears to be no known robust and reliable system or method that can non-invasively determine an indication and/or an assessment of ICP using measured intracranial oxygen saturation and extracranial oxygen saturation such that the proper medical care can be provided to those who may have experienced trauma to the brain.

SUMMARY OF THE INVENTION

In one aspect, a system for non-invasively determining an indication and/or an assessment of intracranial pressure (ICP) is featured. The system includes at least one intracranial light source adapted to be placed on skin above a cranium of a living subject configured to emit light which penetrates the cranium and targets intracranial space of a living subject. At least one extracranial light source is adapted to be placed on skin above a predetermined area of the living subject configured to emit light which penetrates and targets extracranial space of the living subject. A detector subsystem includes at least a first detector configured to detect reflected light from the intracranial space and the light reflected from extracranial space and is configured to output intracranial output signals associated with light detected from the intracranial space and output extracranial output signals associated with the light detected from the extracranial space. A processing subsystem is coupled to the at least one intracranial light source, the at least one extracranial light source, and the detector subsystem. The processing subsystem is configured to determine intracranial oxygen saturation and extracranial oxygen saturation and non-invasively determine an indication and/or an assessment of ICP using a ratio of the intracranial oxygen saturation to the extracranial oxygen saturation.

In one embodiment, the at least one intracranial light source may include at least two light sources. One of the two lights sources may be configured to emit light at one or more first predetermined wavelengths and the oilier of the at least two light sources may be configured to emit light at one or more second predetermined wavelengths. One of the first predetermined wavelengths or the second predetermined wavelengths may be configured to target oxyhemoglobin chromophores and the other of the first predetermined wavelengths or second predetermined wavelengths may be configured to target deoxyhemoglobin chromophores. The at least one extracranial light source may include at least two light sources. One of the two light sources may be configured to emit light at one or more first predetermined wavelengths and the other of the at least two light sources may be configured to emit light at one or more second predetermined wavelengths. The at least one intracranial light source, the at least one extracranial light source, and the at least one detector subsystem may be adapted to be placed on the skin above the cranium of the living subject with the at least one extracranial light source located between the at least one intracranial light source and the at least one first detector. The at least one first detector may be spaced from the at least one intracranial light source by an intracranial separation distance that causes the at least one first detector to detect the light reflected from the intracranial space and output the intracranial output signals. The first detector may be spaced from the at least one extracranial tight source by an extracranial separation distance that causes the at least first detector to detect light reflected from the extracranial space and output the extracranial output signals. The processing subsystem may be configured to alternately enable the at least one intracranial light source and the at least one extracranial light source and alternately enable the first detector to detect the light which reflects from the intracranial space and the light which reflects from the extracranial space to generate the intracranial output signals and the extracranial output signals. The processing subsystem may be responsive to the intracranial output signals and the extracranial output signals and further configured to reduce contributions from the extracranial space which may exist in the intracranial output signals and generate corrected intracranial output signals to increase accuracy of the indication of ICP. The detector subsystem may include a second detector adapted to be placed on one of the predetermined areas of the living subject. The second detector may be placed proximate the at least one extracranial light source and spaced from the at least one extracranial light source by a predetermined extracranial separation distance that causes the second detector to detect light which is reflected from the extracranial space and output the extracranial output signals. The processing subsystem may be coupled to the at least one intracranial light source, the at least one extracranial light source, the first detector, and the second detector. The processing subsystem may be configured to alternately enable the at least one intracranial light source and the at least one extracranial light source and alternately enable the first detector to detect the light reflected from the intracranial space and alternately enable the second detector to detect the light reflected from the extracranial space and generate the intracranial output signals and the extracranial output signals and may be further configured to reduce contributions from the extracranial space that may exist in the intracranial output signals and generate corrected intracranial output signals to increase the accuracy of the indication and assessment of ICP. The intracranial oxygen saturation and/or the extracranial oxygen saturation may include one or more of: oxygen tissue saturation ($StO_2$), arterial oxygen saturation ($SaO_2$), or venous oxygen saturation ($SvO_2$). The system may further include a display device coupled to the processing subsystem configured to display one or more of the indication and/or assessment of ICP, and/or the intracranial oxygen saturation, and/or the extracranial oxygen saturation, and/or a ratio of the intracranial oxygen saturation and the extracranial oxygen saturation, and/or a difference of the intracranial oxygen saturation and the extracranial oxygen saturation.

In another aspect, a system for non-invasively determining an indication and/or an assessment of intracranial pressure is featured. The system includes at least one intracranial light source adapted to be placed on skin above a cranium of a living subject configured to emit light which penetrates a cranium of a living subject and targets intracranial space of the living subject. At least one intracranial detector is placed proximate the at least one intracranial light source and spaced from the intracranial light source by a predetermined intracranial separation distance that causes the intracranial detector to detect the light which reflects from the intracranial space and output intracranial output signals. At least one extracranial light source is adapted to be placed on the skin above a predetermined area of the living subject configured to emit light which penetrates and targets extracranial space of the living subject. At least one extracranial detector is placed proximate the at least one extracranial light source and spaced from the at least one extracranial light source by a predetermined extracranial separation distance that causes the at least one extracranial detector to detect the light which reflects from the extracranial space and output extracranial output signals. A processing subsystem is coupled to the at least one intracranial light source, the at least one intracranial light detector, the at least one extracranial light source senor, and the at least one extracranial detector. The processing subsystem configured to determine intracranial oxygen saturation and extracranial oxygen saturation and non-invasively determine an indication and/or an assessment of ICP using a ratio of the intracranial oxygen saturation to the extracranial oxygen saturation.

In one embodiment, the processing subsystem may be configured to alternately enable the at least one intracranial light source and the at least one extracranial light source and alternately enable the at least one intracranial detector to detect the light reflected from the intracranial space and alternately enable the at least one extracranial detector to detect light which reflects light which reflects from the extracranial space to generate the intracranial output signals and the extracranial output signals. The processing subsystem may be responsive to the intracranial output signals and the extracranial output signals and may be further configured to reduce contributions front the extracranial space which may exist in the intracranial output signals. The processing subsystem may be responsive to the corrected intracranial output signals and the extracranial output signals and may be further configured to determine the intracranial oxygen saturation and the extracranial oxygen saturation and non-invasively determine an indication and/or an assessment of ICP using a ratio of the intracranial oxygen saturation to the extracranial oxygen saturation to increase the accuracy of the indication and/or assessment of ICP. The at least one intracranial light source may include at least two light sources. One of the at least two lights sources may be configured to emit light at one or more first predetermined wavelengths and the oilier of the a least two light sources may be configured to emit light at one or more second predetermined wavelengths. One of the first predetermined wavelengths or the second predetermined wavelengths may be configured to target oxyhemoglobin chromophores and the other of the first predetermined wavelengths or second predetermined wavelengths may be configured to target deoxyhemoglobin chromophores. The at least one extracranial light source may include at least two light sources. One of the at least two light sources may be configured to emit light at one or more first predetermined wavelengths and the other of the at least two light sources configured to emit light at one or more second predetermined wavelengths. One of the first predetermined wavelengths or the second predetermined wavelengths may be configured to target oxyhemoglobin chromophores and the other of the first predetermined wavelengths or second predetermined wavelengths may be configured to target deoxyhemoglobin chromophores. The at least one intracranial detector may be spaced from the at least one intracranial light source by an intracranial separation distance that causes at least one intracranial detector to detect the light reflected from the intracranial space and output the intracranial output signals. The at least one extracranial detector may be spaced from the at least one extracranial light source by an extracranial separation distance that causes the at least one extracranial detector to detect light reflected from the extracranial space and output the extracranial output signals. The intracranial oxygen saturation and/or the extracranial oxygen saturation may include one or more of oxygen tissue saturation ($StO_2$), arterial oxygen saturation ($SaO_2$), or venous oxygen saturation ($SvO_2$). The system may include a display device coupled to the processing subsystem configured to display one or more of: the indication and/or assessment of ICP, and/or the intracranial oxygen saturation, and/or the extracranial oxygen saturation, and/or the ratio of the intracranial oxygen saturation and the extracranial oxygen saturation, and/or a difference of the intracranial oxygen saturation and the extracranial oxygen saturation.

In yet another aspect, a method for non-invasively determining an indication and/or an assessment of intracranial pressure by measuring oxygen saturation is featured. The method includes emitting light which penetrates a cranium of a living subject and targets intracranial space of the living space, emitting light which penetrates and targets extracranial space of a predetermined area of the living subject, detecting light reflected from the intracranial space outputting intracranial output signals, and detecting light reflected from the extracranial space and outputting extracranial output signals. The method also includes responding to the intracranial output signals and the extracranial output signals and determining intracranial oxygen saturation and extracranial oxygen saturation and non-invasively and determining an indication and/or an assessment of ICP using a ratio of the intracranial oxygen saturation to the extracranial oxygen saturation.

In one embodiment, emitting light which penetrates the cranium of the living subject and targets the intracranial space may include emitting light at one or more first predetermined wavelengths and emitting light at one or more second predetermined wavelengths. One or more of the first predetermined wavelengths may be configured to target oxyhemoglobin chromophores and the other of the one or more first predetermined wavelengths or second predetermined wavelengths may be configured to target deoxyhemoglobin chromophores. Emitting light which penetrates and targets the extracranial space of the living subject may include emitting light at one or more first predetermined wavelengths and emitting light at one or more second predetermined wavelengths. One of the one or more first predetermined wavelengths may be configured to target oxyhemoglobin chromophores and the other of the one or more first predetermined wavelengths or one or more second predetermined wavelengths may be configured to target deoxyhemoglobin chromophores. The method may include alternately emitting light which penetrates the cranium of the living subject and targets the intracranial space of the living subject and emitting light which penetrates and targets the extracranial space of the predetermined area of the living subject and alternately detecting tight reflected from the intracranial space and outputting the extracranial signals and alternately detecting light reflected from the extracranial space and outputting the extracranial signals and reducing contributions from the extracranial space that may exist in the intracranial output signals in generating corrected intracranial output signals to increase the accuracy of the indication and/or assessment of ICP.

The subject invention, however, in other embodiments, need not achieve all these objectives and the claims hereof should not be limited to structures or methods capable of achieving these objectives.

BRIEF DESCRIPTION OF THE SEVERAL VIEWS OF THE DRAWINGS

Other objects, features and advantages will occur to those skilled in the art from the following description of a preferred embodiment and the accompanying drawings, in which.

DETAILED DESCRIPTION OF THE INVENTION

Figure 1:
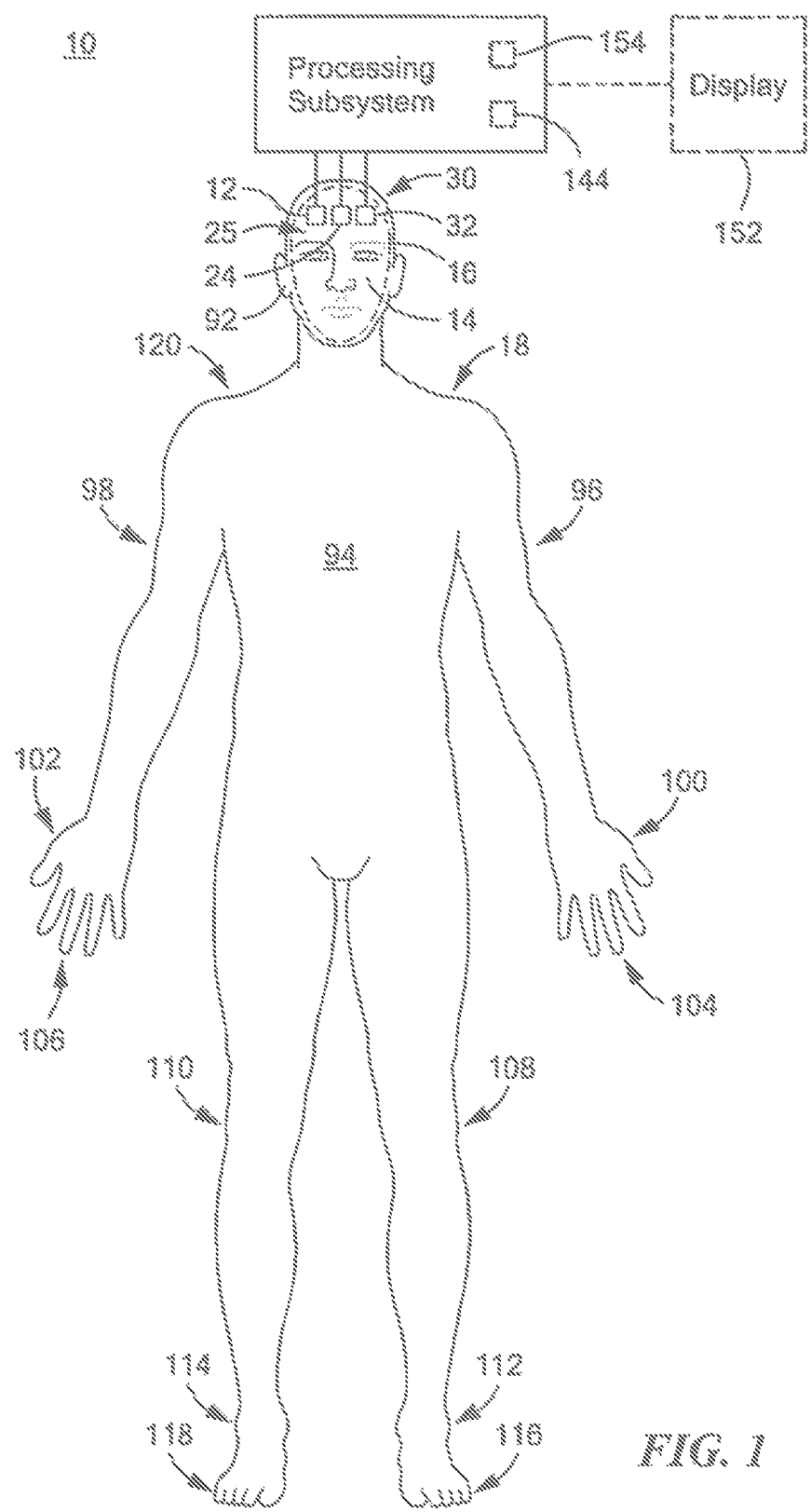
FIG. 1 is a schematic block diagram showing the primary components of one example of the system for non-invasively determining an indication and/or an assessment of ICP shown in place above the cranium of a living subject.

Aside from the preferred embodiment or embodiments disclosed below, this invention is capable of other embodiments and of being practiced or being carried out in various ways. Thus, it is to be understood that the invention is not limited in its application to the details of construction and the arrangements of components set forth in the following description or illustrated in the drawings. If only one embodiment is described herein, the claims hereof are not to be limited to that embodiment. Moreover, the claims hereof are not to be read restrictively unless there is clear and convincing evidence manifesting a certain exclusion, restriction, or disclaimer.

Conventional optical sensing systems, particularly those using near infrared (NIR) light, have been used to monitor both blood volume oscillations and blood oxygen content by using a light source and detector placed on the skin. In brain related applications, near infrared spectroscopy (NIRS) may be used to detect changes in oxygenation attributed to regional brain activity or to infer information associated with cerebral blood flow and cerebral blood volume and evaluate basic brain functions. See, e.g., Megumi Mizuno et al., *A Functional NIRS Study of Brain Functional Networks Induced by Social Time Coordination*, Brain Sci., 9, 43 (2019), incorporated by reference herein. If near infrared light is highly sensitive to the oxygen saturation of hemoglobin, then its large penetration depth inside tissue implies that the arterial, venous, and capillary compartments all contribute to the optical signal. The average hemoglobin oxygenation measured with NIRS is often referred to as oxygen tissue saturation ($StO_2$). See, e.g., Olsson et al.,

*Regional Cerebral Saturation Monitoring with Near-Infrared Spectroscopy During Selective Antegrade Cerebral Perfusion: Diagnostic Performance and Relationship to Postoperative Stroke*, The Journal of Thoracic and Cardiovascular Surgery, Vol. 131, No. 2 (February 2006), incorporated by reference herein. $StO_2$ values are assumed to be in between arterial saturation ($SaO_2$) and local venous saturation ($SvO_2$) values. The contribution of the arterial compartment to the non-invasive optical signal can be isolated because of its unique temporal dynamics associated with the systolic-diastolic blood pressure at the heartbeat frequency, thus allowing $SaO_2$ retrieval. $SvO_2$ can be estimated by isolating the oscillatory components at the respiratory frequency as a result of the so-called respiratory pump that makes the venous blood volume oscillate at the respiratory frequency. See e.g., Franceschini et al., *Near-Infrared Spiroximetry: Noninvasive Measurements of Venous Saturation in Piglets and Living Subjects*, J. Appl. Physiol., 92 (1) (1985), incorporated by reference herein. $SaO_2$ is known to reflect information about the ventilation and oxygen exchange in lungs while $SvO_2$ is a parameter that reflects the local balance between blood flow and oxygen consumption. See e.g., Franceschini et al., cited supra. Therefore, measuring intracranial (cerebral) oxygen saturation and extracranial (extracerebral) oxygen saturation and determining a ratio of intracranial (cerebral) oxygen saturation to extracranial (extracerebral) oxygen saturation may provide a unique avenue into cerebral hemodynamics that have been impacted by ICP thus providing means for determining of an indication and/or assessment of ICP, as discussed in detail below.

There is shown in FIG. 1 one embodiment of system 10 for non-invasively assessing ICP by measuring oxygen saturation. System 10 includes at least one intracranial or cerebral light source 12 adapted to be placed on skin 14 above cranium 16 of living subject 18. Cranium 16 is shown in phantom in greater detail in FIG. 2. At least one intracranial light source 12, FIGS. 1 and 2 emits light 20, shown in greater detail in FIG. 3, which penetrates cranium 16 and targets intracranial space 22 as shown. Intracranial space 22 of cranium 16 includes at least brain 23, FIG. 2, of living subject 18. Brain 23 includes, inter alia, the cerebrum, the cerebellum, and the like, as known by those skilled in the art. In this example, living subject 18 is a human subject. In other examples, living subject 18 may be any type of living animal that may experience ICP.

Figure 2:
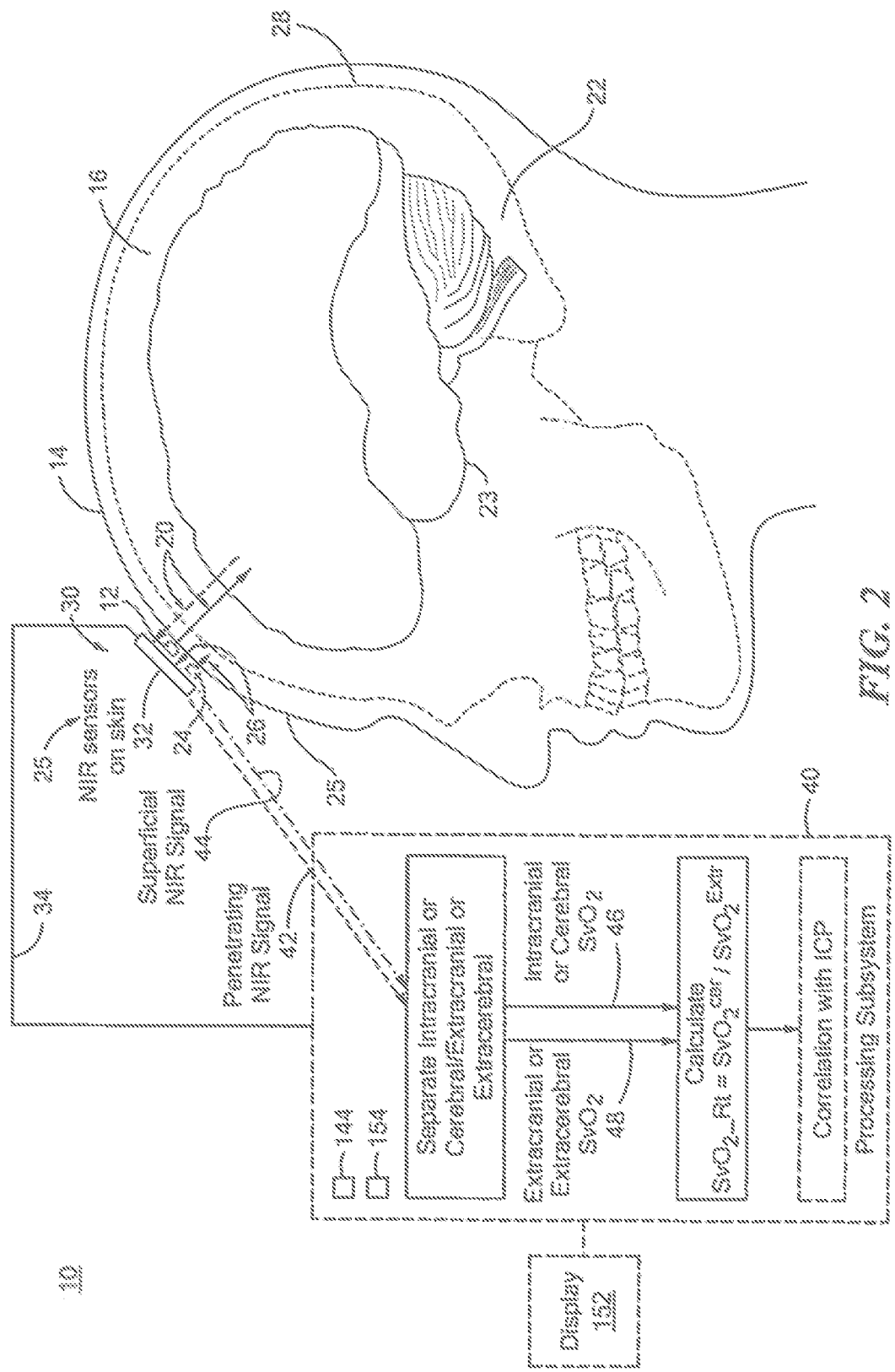
FIG. 2 is a schematic block diagram showing in further detail the intracranial light source and the extracranial light source shown in FIG. 1.
Figure 3:
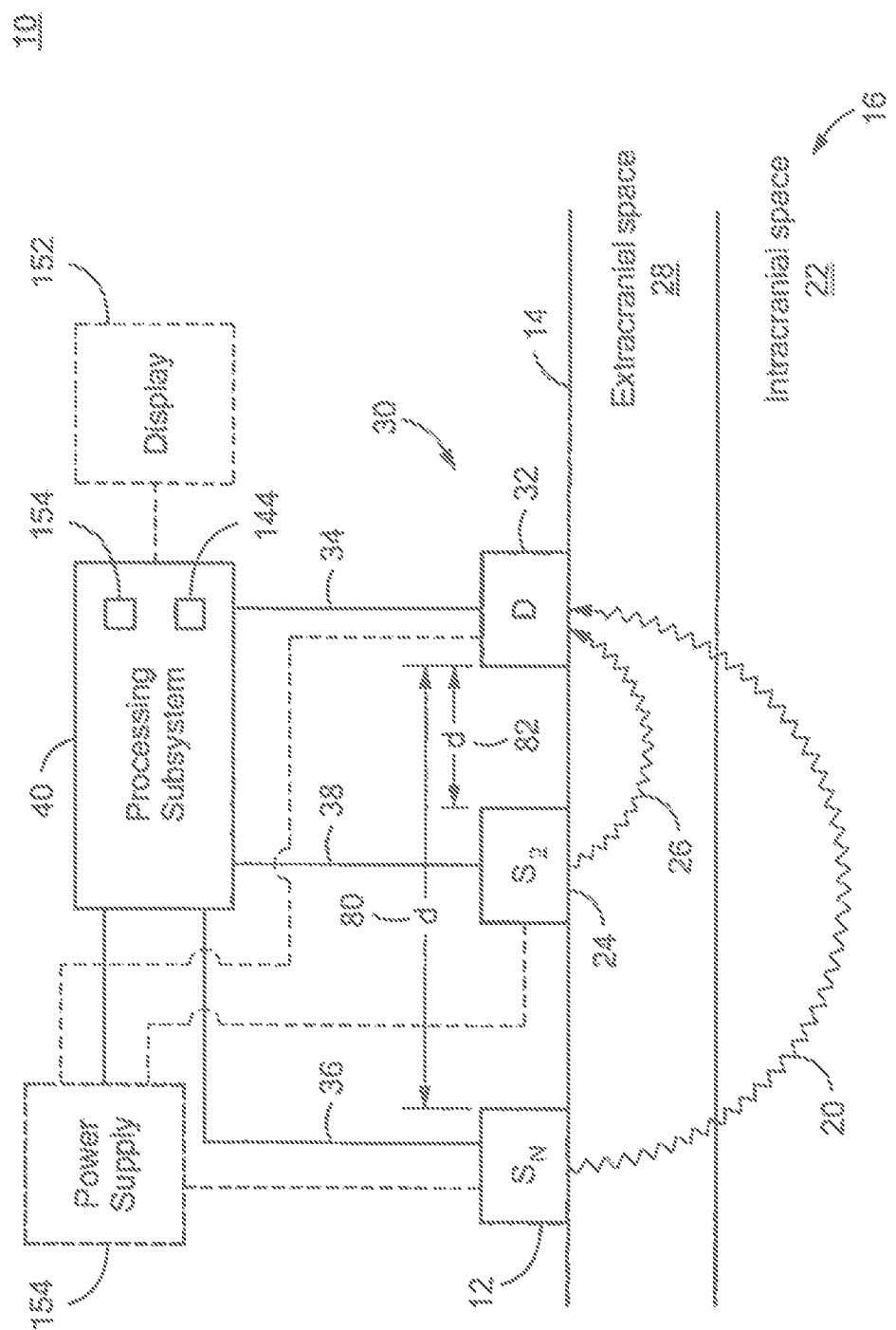
FIG. 3 is a schematic block diagram showing in further detail one example of the spacing of the intracranial light source, the extracranial light source, and the detector shown in FIGS. 1 and 2.

System 10, FIGS. 1-3, also includes at least one extracranial or extracerebral light source 24, FIGS. 1-3, adapted to be placed on skin 14 above a predetermined area of the living subject. In this example, the predetermined area of living subject 18, FIG. 1, is skin 14 above cranium 16, e.g., on forehead 25. FIGS. 1 and 2. At least one extracranial light source 24 may also be adapted to be placed on the skin of any desired predetermined area of living subject 18, e.g., ear 92, FIG. 1, torso 94, either of arms 96,98, either of hands 100, 102, any of fingers 104, 106, either of legs 108, 110, any of toes 116, 118, or back 120, as discussed in further detail below. At least one extracranial light source 24 emits light 26, FIGS. 2-3, which penetrates and targets extracranial space 28 of living subject 18 as shown.

System 10, FIGS. 1-3, also includes detector subsystem 30 including at least first detector 32 which detects reflected light 20, FIGS. 2-3, from intracranial space 22 and reflected light 26 from extracranial space 28. First detector 30 also outputs intracranial output signals associated with light 20 detected from intracranial space 22 and extracranial output signals associated with light 26 detected from extracranial space 28.

In one example, at least one intracranial light source 12 FIGS. 1-3, and/or at least one extracranial light source 24 preferably includes one or more of a near infrared (NIR) light source, at least one light emitting diode (LED), and/or an array of photodiodes or phototransistors.

System 10 also includes processing subsystem 40 coupled to at least one intracranial light source 12, e.g., by line 36, FIG. 3, at least one extracranial light source 24 by line 38, and detector subsystem 30 with first detector 32 by line 34 as shown. Processing subsystem 40, FIGS. 1-3, is configured to non-invasively determine intracranial oxygen saturation and extracranial oxygen saturation (See e.g., Yanagisawa et al., *Partial Optical Path Length in the Scalp in Subject-Specific Head Models For Multi-Distance Probe Configuration of Near Infrared Spectroscopy*, Proceedings Volume 10711, Biomedical Imaging and Sensing Conference, (2018), incorporated by reference herein) and non-invasively determine an indication and/or an assessment of ICP using a ratio of the intracranial oxygen saturation to the extracranial oxygen saturation, as discussed in further detail below.

$StO_2$ requires quantitative measurements of oxyhemoglobin and deoxyhemoglobin concentration. $SaO_2$ and $SvO_2$ can be calculated by either having access to quantitative measurements of oxyhemoglobin and deoxyhemoglobin concentration or from measuring the amplitude of the optically measured oxyhemoglobin and deoxyhemoglobin concentration oscillations by detector subsystem 30 preferably including first detector 32 at the cardiac and respiratory frequency respectively. Oscillatory components of oxyhemoglobin and deoxyhemoglobin concentration at the bean rate and breathing rate are mostly representative of the arterial and venous compartments. See, e.g., Franceschini et al., cited supra. Processing subsystem 40 preferably performs basic signal processing for oxyhemoglobin and deoxyhemoglobin concentration calculation. See, e.g., Franceschini el al., cited supra, and Franceschini et al., *Noninvasive Optical Method of Measuring Tissue and Arterial Saturation: An Application to Absolute Pulse Oximetry of the Brain*, Opt. Lett. 24(12) (1999), incorporated by reference herein, and/or to extrapolate the predetermined frequency components of interest (cardiac and breathing rate) in order to use hemoglobin concentration oscillations for saturation calculation purposes.

FIG. 2 shows one example of the intracranial or cerebral (Penetrating NIR Signal) output signals, indicated at 42, also referred to herein as Cerebral ($SvO_2$) output signals, output by first detector 32 in response to reflected light 20 also shown in FIG. 3, detected from intracranial space 22 and extracranial or extracerebral (Superficial NIR signal) output signals, indicated at 44 FIG. 3, also referred to as Extracerebral ($SvO_2$) output signals, output by first detector 32 in response to reflected light 26 detected from extracranial space 28. Processing subsystem 40 preferably separates the extracranial contribution from the intracranial signals for each wavelength then computes intracranial or cerebral $SvO_2$ and extracranial or extracerebral $SvO_2$, indicated at 46, 48, respectively.

In this example, processing subsystem 40 non-invasively determines an indication and/or an assessment of ICP using a ratio of the intracranial oxygen saturation to the extracranial oxygen saturation using equation (1):

$$SvO_2\_Rt = SvO_2^{CER}/SvO_2^{EXTRA} \qquad (1)$$

where $SvO_2\_Rt$ is the oxygen saturation ratio, $SvO_2^{CER}$ is the cerebral or intracranial oxygen saturation and $SvO_2^{EXTRA}$ is the extracerebral or extracranial oxygen saturation. Processing subsystem may use venous oxygen saturation, arterial oxygen saturation, or a combination of both. Thus, processing subsystem preferably non-invasively determines an indication and/or an assessment of ICP using the ratio of the intracranial oxygen saturation to the extracranial oxygen saturation shown generally in equation (2) below:

$$\text{Ratio} = (\text{intracranial oxygen saturation})/(\text{extracranial oxygen saturation}) \quad (2)$$

In another example processing subsystem 40 may non-invasively determine an indication and/or an assessment of ICP using equation (3) below:

$$ICP = K_1*(\text{Ratio}) + K_2*(\text{intracranial oxygen saturation}) + K_3*(\text{extracranial oxygen saturation}) + K_4 \quad (3)$$

where $K_1$, $K_1$ and $K_3$ are positive or negative constants and $K_4$ is an offset. Thus, depending on the sign of $K_2$ and $K_3$ (positive or negative), equation (3) covers difference as well as the addition of the intracranial oxygen saturation and the extracranial oxygen saturation.

In one example, the determination of ICP may be achieved by using a mathematical function that relates ICP to the oxygen saturation ratio or by implementing characteristic curves (or look up table) that which hold a sequence of ratio values and an ICP value for each. In cases where a specified ratio value is found to be between two ICP values in the characteristic curve, interpolation techniques can be applied between the closest ratio values on the curve, above and below the specified ratio value, as known to one skilled in the art.

In yet another example, processing subsystem 40 may non-invasively determine an indication and/or an assessment of ICP using a non-linear function of the ratio defined in equation (2), the intracranial oxygen saturation and the extracranial oxygen saturation, such as an exponential function or a function derived by curve-fitting representative data.

In one design, at least one intracranial light source 12, FIGS. 1-3, and/or at least one extracranial light source 24 preferably emit light having a wavelength in the range of about 500 nm to about 1,000 nm. In other examples, at least one intracranial light source 12 and/or at least the extracranial light source 24 may emit light having wavelengths greater or less than the range of about 500 nm to 1,000 nm as known by those skilled in the art.

Figure 4:
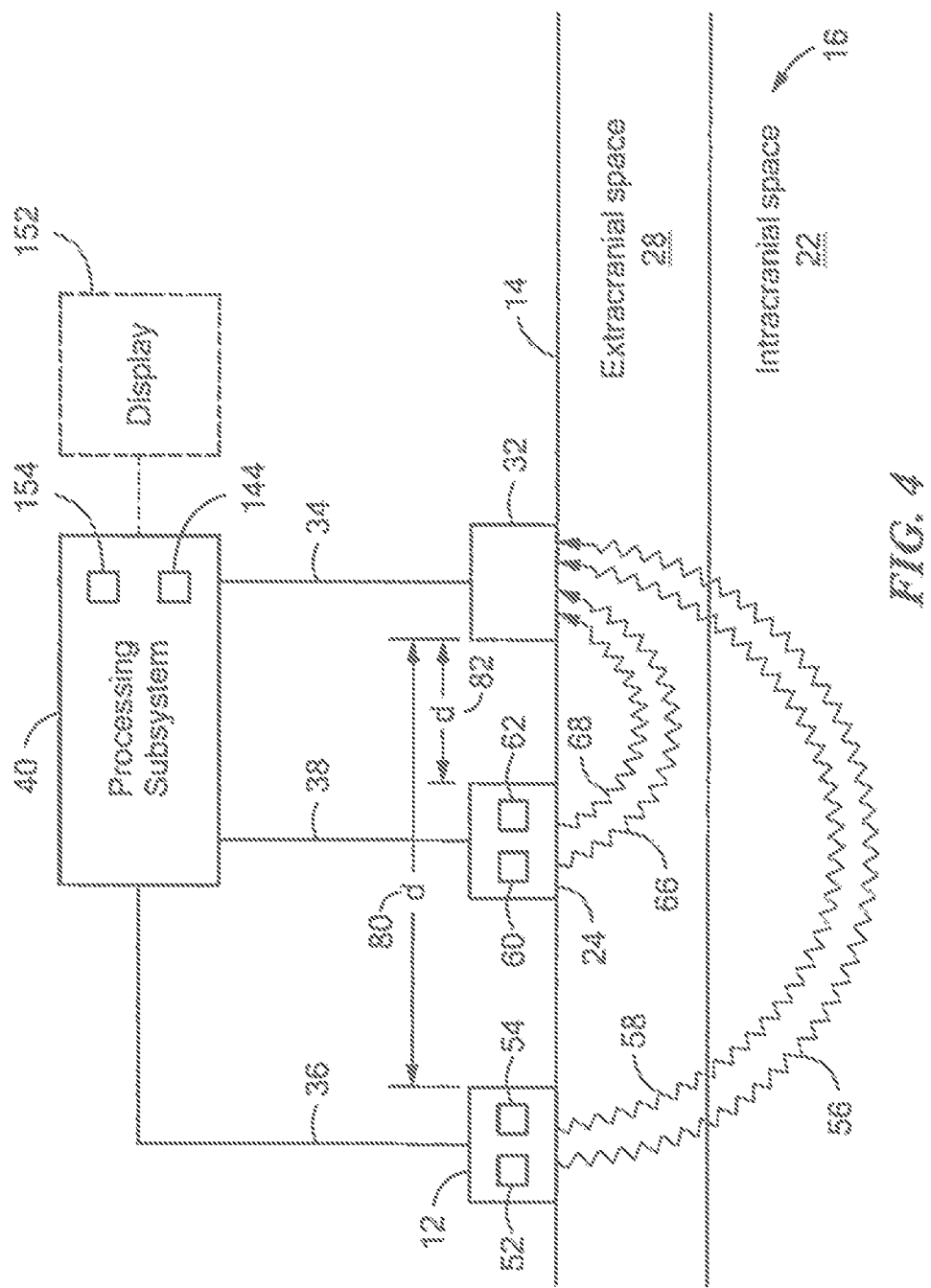
FIG. 4 is a schematic block diagram showing one example of the intracranial light source and the extracranial light source shown in one or more of FIGS. 1-3 each including at least two light sources.

In one example, at least one intracranial light source 12 preferably includes at least two light sources, e.g., intracranial light source 52, FIG. 4, where like parts have been given like numbers, and intracranial light source 54. One of intracranial light sources 52 or 54 preferably emits light at one or more first predetermined wavelengths, e.g., at about 690 nm, and the other of intracranial light sources 52 and 54 preferably emits at one or more second predetermined wavelengths, e.g., at about 830 nm. Other one or more first and second predetermined wavelengths may also be utilized as known by those skilled in the art. In this example. Intracranial light source 52 preferably emits light 56 at the first predetermined wavelength and intracranial light source 54 preferably emits light 58 at the second predetermined wavelength which are both detected by first detector 32 as shown. Preferably, one of the first predetermined wavelengths or the second predetermined wavelengths targets oxyhemoglobin chromophores and the other of the first or second predetermined wavelengths targets the deoxyhemoglobin chromophores, as known by those skilled in the art. See, e.g., Zhao et al., *Optimal Hemoglobin Extinction Coefficient Data Set For Near-Infrared Spectroscopy*, Biomed Optical Express, 8(11) (2017), incorporated by reference herein.

Similarly, at least one extracranial light source 24, FIGS. 1-3, may also preferably include at least two light sources, e.g., extracranial light source 60, FIG. 4, and extracranial light source 62. One of extracranial light sources 60 or 62 preferably emits light at one or more first predetermined wavelengths, e.g., at about 690 nm, and the other of extracranial light sources 60 and 62 preferably emits at one or more second predetermined wavelengths, e.g., at about 830 nm. Additional first and second predetermined wavelengths other than the wavelengths discussed above may also be utilized as known by those skilled in the art. In this example, light source 60 preferably emits light 66 at the first predetermined wavelength and light source 62 preferably emits light 68 at the second predetermined wavelength which are both detected by detector 32 as shown. Preferably, one of the first or second predetermined wavelengths targets oxyhemoglobin chromophores and the other of the first or second predetermined wavelengths targets the deoxyhemoglobin chromophores, as known by those skilled in the art.

In one example, at least one intracranial light source 12 shown in one or more of FIGS. 1-4, may be adapted to be placed on skin 14 above cranium 16 of living subject 18 with the at least one extracranial light source 24 located between at least one intracranial light source 12 and first detector 32, e.g., as shown in FIGS. 3 and 4.

In one example, first detector 32 shown in one or more of FIGS. 1-4 is preferably spaced from at least one intracranial light source 12 by intracranial separation distance d-80, FIGS. 3 and 4, that causes first detector 32 to detect light 20, FIGS. 2 and 3, or light 56, 58, FIG. 4, reflected from intracranial space 22 and output the intracranial output signals to processing subsystem 40. Similarly, first detector 32 may be spaced from extracranial light source 24 by extracranial separation distance d-82, FIGS. 3 and 4, that causes first detector 32 to detect light 26. FIGS. 2 and 3, or light 66, 68, FIG. 4, reflected from extracranial space 28 and output the extracranial output signals to processing subsystem 40.

In one design, processing subsystem 40, FIGS. 1-4, preferably enables at least one intracranial light source 12 and at least one extracranial light source 24 and alternately enables first detector 32 to detect light 20, FIGS. 2 and 3, or light 56, 58. FIG. 4, which reflects from intracranial space 22 and light 26. FIGS. 2 and 3, or light 66, 68, FIG. 4, which reflects from extracranial space 28 and generate the intracranial output signals and extracranial output signals, respectively. Processing subsystem 40 is also preferably responsive to the intracranial output signals and the extracranial output signals and preferably reduces contributions from extracranial space 28 which may exist in the intracranial output signals and generate corrected intracranial output signals to increase the accuracy of the indication of ICP.

In one example, the intracranial oxygen saturation, e.g., cerebral oxygen saturation and/or the extracranial oxygen saturation includes one or more of oxygen tissue saturation ($StO_2$), arterial oxygen saturation ($SaO_2$), or venous oxygen saturation ($SvO_2$).

As discussed above with reference to one or more of FIGS. 1-4, at least one extracranial light source 24 is shown adapted to be placed on skin 14 above the predetermined area of the living subject 18 depicted as cranium 16. In other examples, system 10', FIG. 5, where like parts have been given like numbers, preferably includes extracranial light source 24 adapted to be placed on the skin above of any desired predetermined area of living subject 18, e.g., ear 92, torso 94, either of arms 96, 98, either of hands 100, 102, any of fingers 104, 106, either of legs 108, 110, any of toes 116, 118, or back 120 of living subject 18, as exemplarily shown in FIG. 5.

Figure 5:
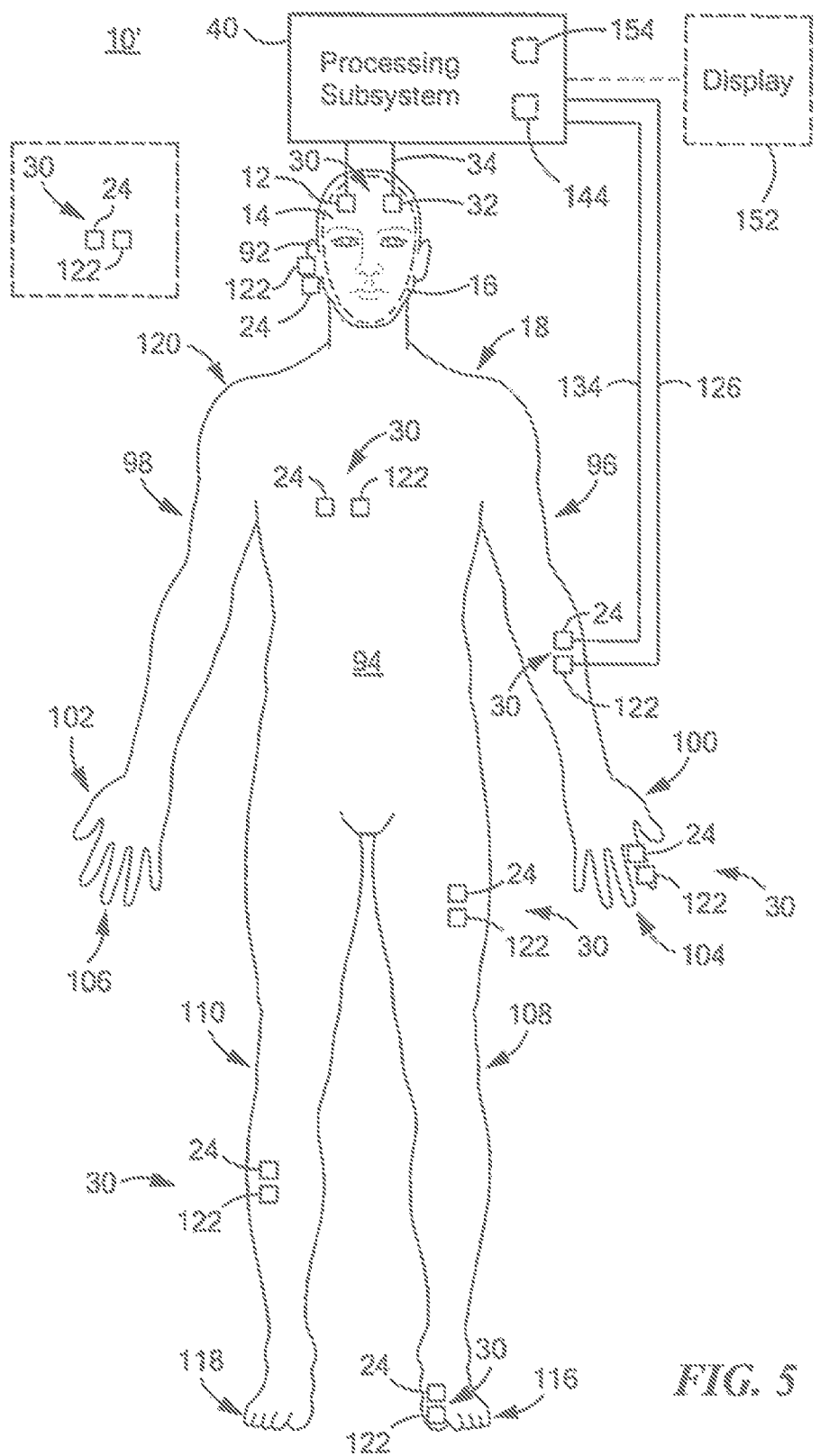
FIG. 5 is a schematic block diagram showing examples of additional locations for the placement of the extracranial light source on a living subject.

When at least one extracranial light source 24 is placed on a predetermined area other than cranium 16, e.g., any of predetermined areas 92-120 discussed above, detector subsystem 30 preferably includes second detector 122 adapted to be placed proximate the location of extracranial light source 24 placed at the predetermined location other than cranium 16, e.g., as exemplarily shown in FIG. 5. In this design, second detector 122 may also be referred to as extracranial detector 122. In this example, first detector 32 located on skin 14 above cranium 16 is responsive only to light 20, FIG. 7, reflected from intracranial space 22 emitted by at least one intracranial light source 12 as discussed below. First detector 32 may also be referred to herein as intracranial detector 32.

In this example, at least one extracranial light source 24, FIG. 5, is shown placed on the skin above arm 96 and coupled to processing subsystem 40 by line 134. Second or extracranial detector 122 is placed proximate at least one extracranial light source 24 as shown and is couple to processing subsystem 40 by line 126. In other examples, at least one extracranial light source 24 and second or extracranial detector 122 may be placed proximate each other on any of predetermined area 92-120 as discussed above and as exemplarily shown, and similarly coupled to processing subsystem 40.

Figure 6:
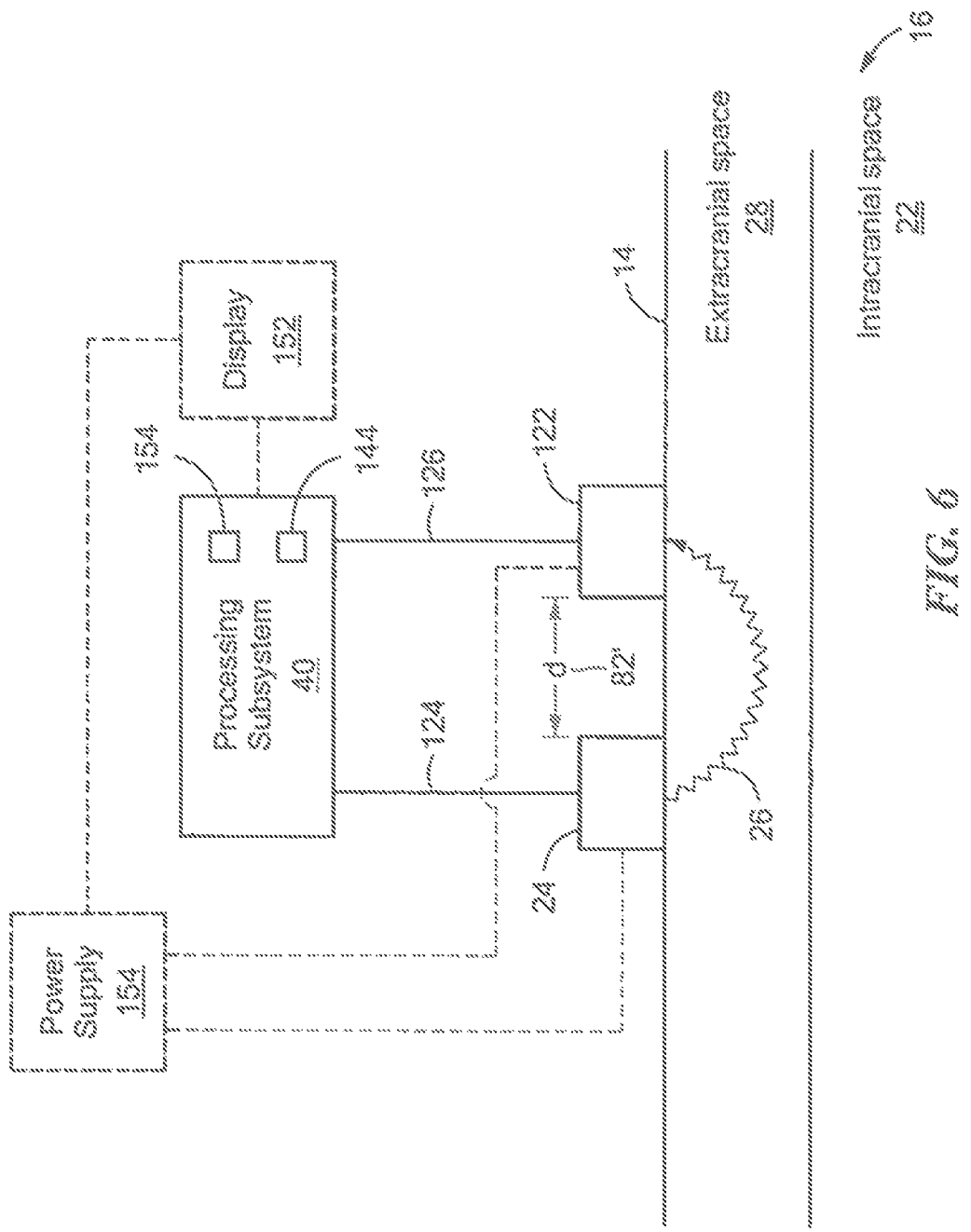
FIG. 6 is a schematic block diagram showing in further detail one example of the spacing of the extracranial light source and the detector shown in FIG. 5.

Similar as discussed above with reference to one or more of FIGS. 1-4, at least one extracranial light source 24, FIG. 5, located at any of predetermined areas 92-120, emits light 26. FIG. 6, which penetrates and targets extracranial space 28 of the predetermined area where at least one extracranial light source is located. Second or extracranial detector 122 located proximate at least one extracranial light source 24 detects reflected light 26 from extracranial space 22 and outputs extracranial output signals associated with light 26 detected from extracranial space 28 to processing subsystem 40.

Similar as discussed above, with reference to one or more of FIGS. 1-4, system 10' includes at least one intracranial light source 12, FIG. 5, adapted to be placed on skin 14 above cranium 16. At least one intracranial light source 12, FIGS. 5 and 7, emits tight 20, FIG. 7, which penetrates cranium 16 (shown in greater detail in FIG. 2) and targets intracranial space 22. First or intracranial detector 32, FIGS. 5 and 7, detect reflected light 20 from intracranial space 22 outputs intracranial output signals associated with light 20 detected from intracranial space 22 to processing subsystem 40.

Figure 7:
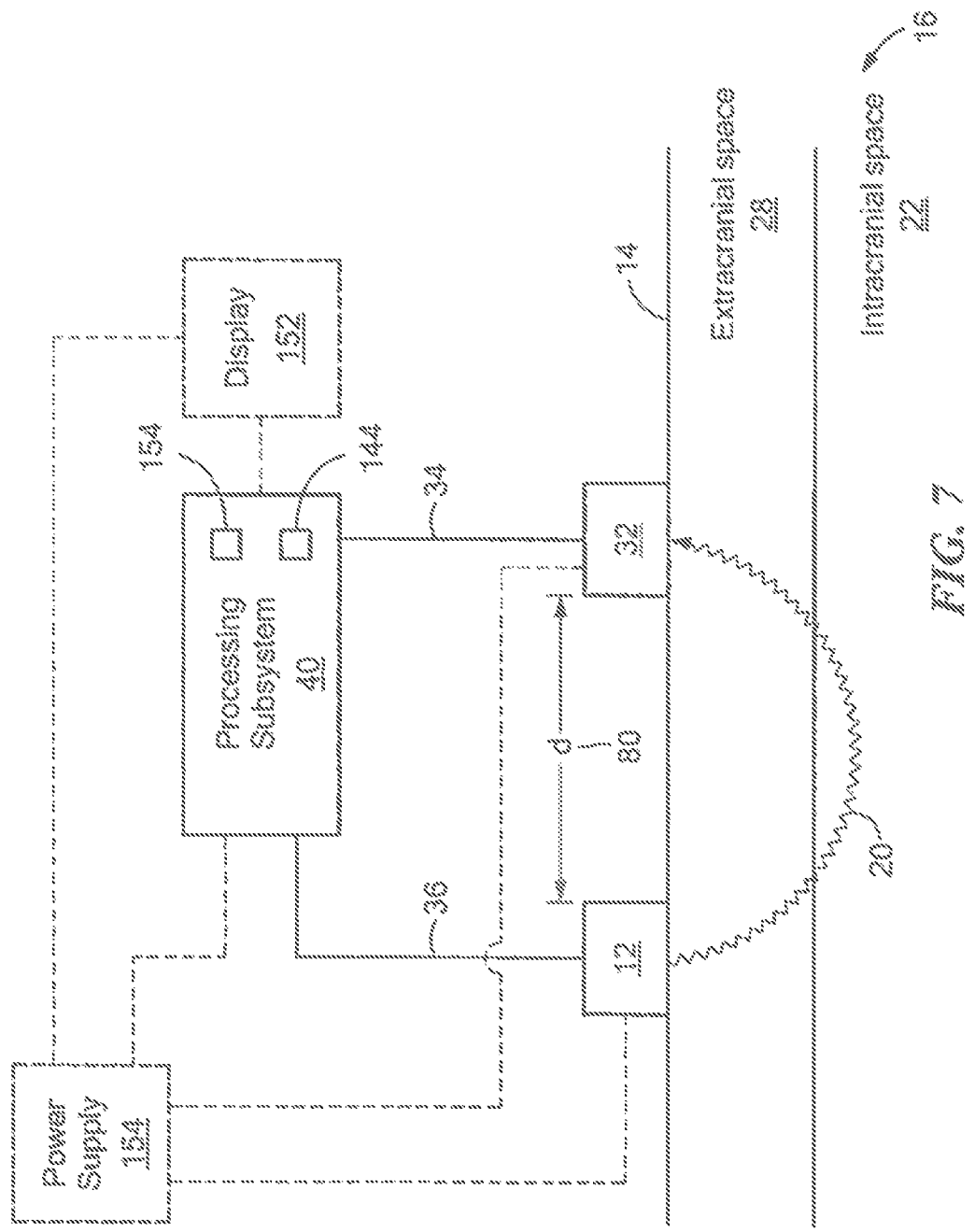
FIG. 7 is a schematic block diagram showing in further detail one example of the spacing of the intracranial light source and the detector shown in FIG. 5.

Processing subsystem 40, FIGS. 5-7 is preferably coupled to at least one intracranial light source 12, at least one extracranial light source 24, first or intracranial detector 32 and second or extracranial detector 122 as shown and is responsive to intracranial output signals and extracranial output signals. Similar as discussed above with reference to one or more of FIGS. 1-4, processing subsystem 40, FIGS. 5-7, is preferably configured to determine intracranial oxygen saturation and extracranial oxygen saturation non-invasively determine an indication and/or an assessment of ICP using a ratio of the intracranial oxygen saturation to the extracranial oxygen saturation.

Figure 8:
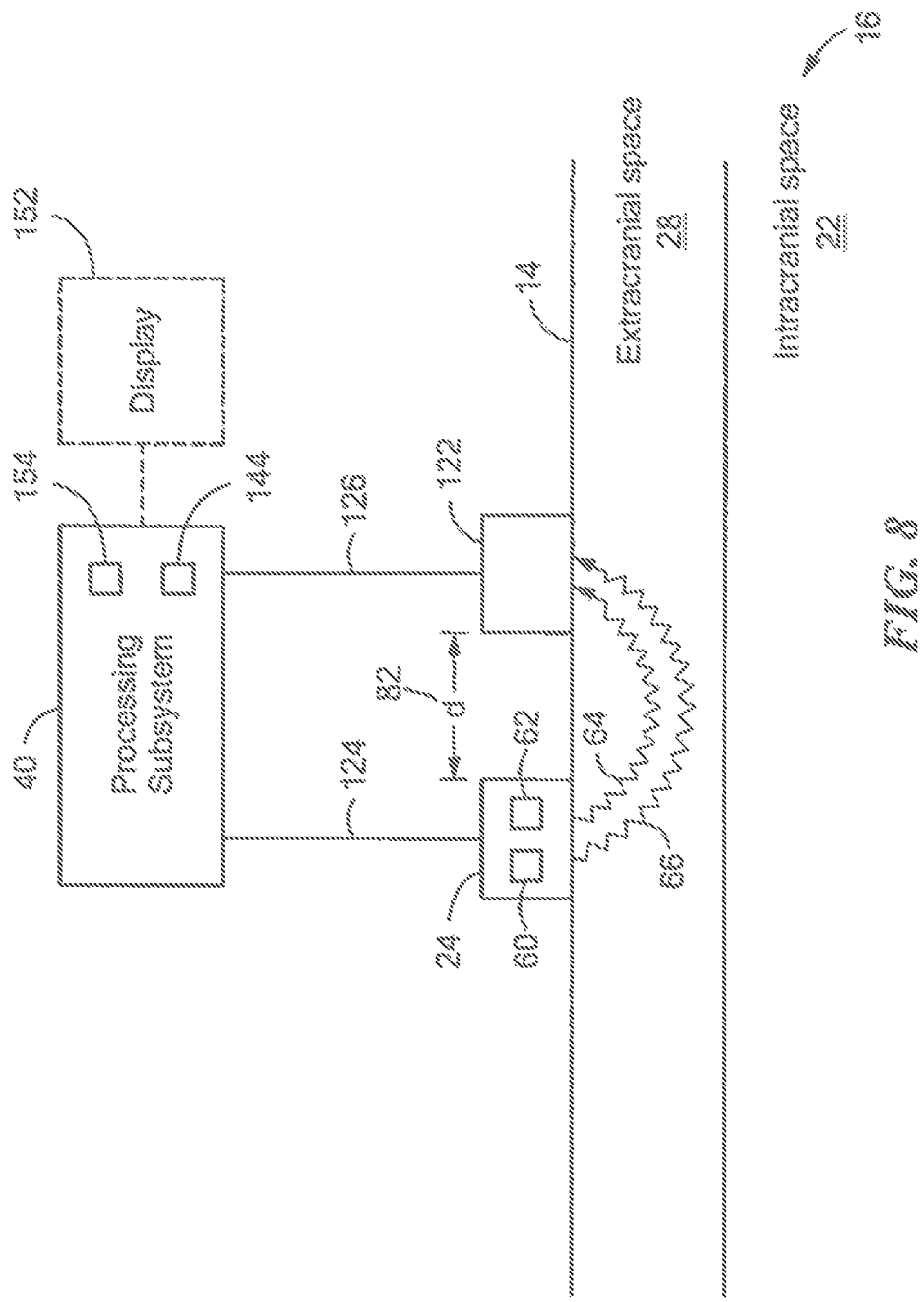
FIG. 8 is a schematic block diagram showing one example of the extracranial light source shown FIG. 5 including at least two light sources.

Extracranial light source 24, FIGS. 5 and 6, placed on any of predetermined area 92-120, FIG. 5, of living subject 18 discussed above may include at least two light sources, e.g., extracranial light source 60, FIG. 8, and extracranial light source 62 which operate similar as discussed above with reference to at least FIG. 4 to preferably emit light 64, 66 at one or more first and second predetermined wavelengths.

Figure 9:
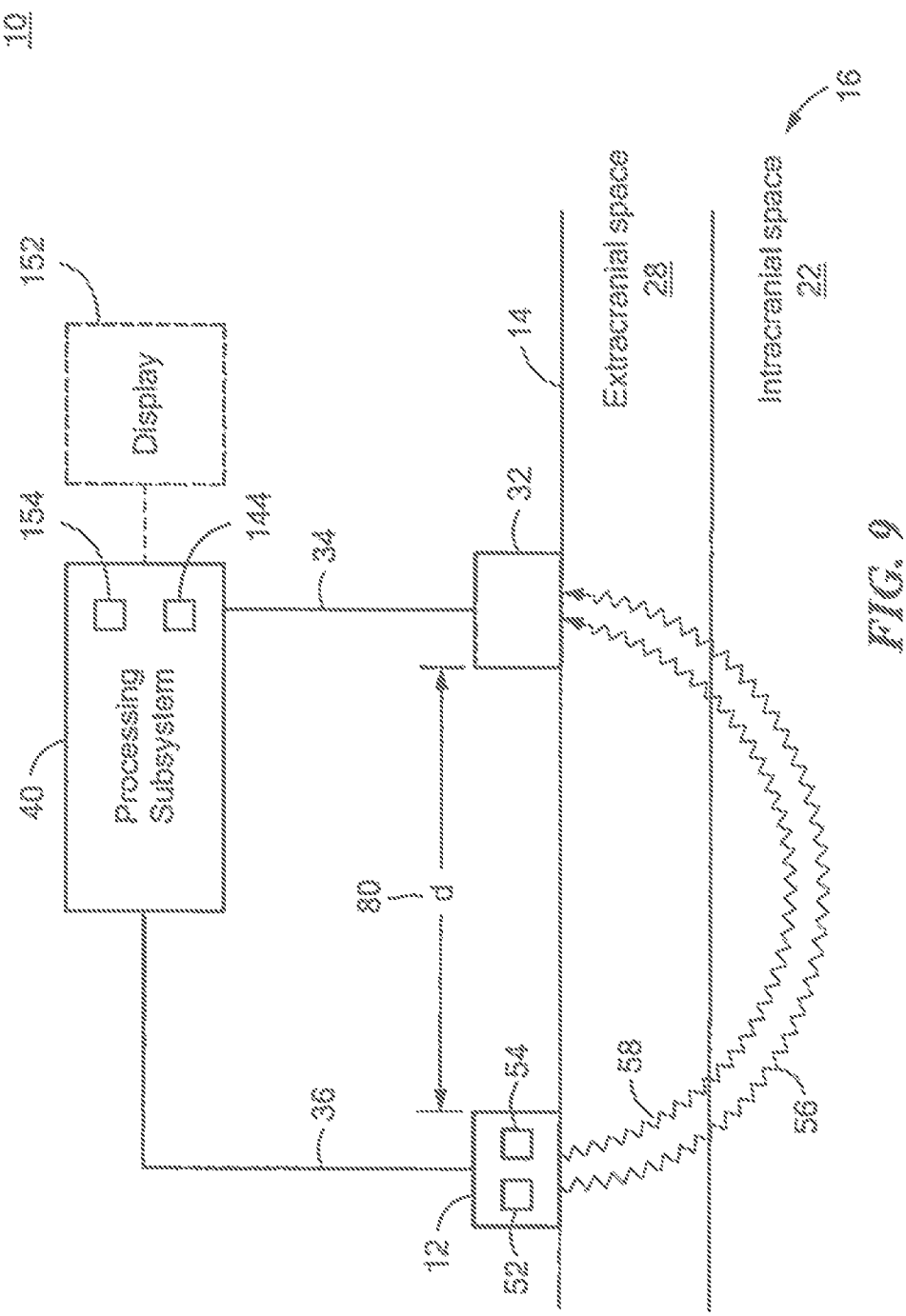
FIG. 9 is a schematic block diagram showing one example of the intracranial light source shown FIG. 5 including at least two light sources.

At least one intracranial light source 12, FIGS. 5 and 7, placed on the skin above cranium 16 may also include at least two light sources, e.g., first light source 52, FIG. 9, and second light source 54 which operate similar as discussed above with reference to at least FIG. 4 to preferably emit light 56, 58 at one or more first and second predetermined wavelengths.

Similar as discussed above with reference to one or more of FIGS. 1-4, first or intracranial detector 32, FIGS. 5, 7 and 9, is preferably spaced from at least one intracranial light source 12 by intracranial separation distance d-80, FIGS. 7 and 9, that causes first or intracranial detector 32 to detect light 20, FIG. 7, or light 56,58, FIG. 9, reflected from intracranial space 22 and output the intracranial output signals to processing subsystem 40.

Second or extracranial detector 122, FIGS. 5,6 and 8, is also preferably spaced from at least one extracranial light source 24 by predetermined extracranial separation distance d-82, FIGS. 6 and 8, that causes second detector 122 to detect light 26, FIG. 6 or light 64, 66, FIG. 8, which is reflected from extracranial space 28 located at any of predetermined areas 92-120, FIG. 5, in this example arm 96, and output extracranial output signals, e.g., by line 126, FIGS. 6 and 8 to processing subsystem 40. Although in this example second or extracranial detector 122 is placed proximate extracranial light source 24 located on arm 96 of living subject 18, in other examples, second detect or 122 may be placed on any of the predetermined areas 92-120 discussed above and shown in FIG. 5 and predetermined extracranial separation distance, d-82, is preferably determined in a similar manner.

Similar as discussed above with reference to one or more of FIGS. 1-4, processing subsystem 40, FIGS. 5-9, preferably alternately enables at least one intracranial light source 12 and at least one extracranial light source 122 and alternately enables first or intracranial detector 32 to detect light reflected from intracranial space 22 and alternately enable second or extracranial detector 122 to detect light 26 reflected from extracranial space 28 and generate the intracranial output signals and the extracranial output signals. Processing subsystem 40 also preferably reduces contributions from extracranial space 28, FIGS. 6-9, which may exist in the intracranial output signals and generate corrected intracranial output signals to increase the accuracy of the indication of ICP.

Processing subsystem 40 shown in one ore more of FIGS. 1-8 may include one or more processors, e.g., processor 42. Processing subsystem 40 may also be configured as an application-specific integrated circuit (ASIC), firmware, hardware, and/or software (including firmware, resident software, micro-code, and the like) or a combination of both hardware and software that may all generally be referred to herein as "processing subsystem 40". Computer program code for the programs for carrying out the instructions or operation of processing subsystem 40 may be written in any combination of one or more programming languages, including an object-oriented programming language, e.g., C++, Smalltalk, Java, and the like, or conventional procedural programming languages, such as the "C" programming language or similar programming languages.

The determined indication and/or an assessment of ICP discussed above with reference to one or more of FIGS. 1-9 is not an actual measured ICP which is typically measured in mmHg. Instead, tire indication and/or assessment of ICP is calculated or determined using the ratio of the measured intracranial or cerebral oxygen saturation to the measured extracranial or extracerebral oxygen saturation discussed above is preferably displayed on a device, e.g., display device 152, e.g., a monitor of a personal computer, a smart device, such as smart phone or tablet, or similar type device. Display device 152 preferably displays one or more of the indication and/or assessment of ICP, the intracranial or cerebral oxygen saturation and/or the extracranial or extracerebral oxygen saturation and/or a ratio and/or difference of the intracranial or cerebral oxygen saturation and the extracranial or extracerebral oxygen saturation as discussed above.

System 10, 10' shown in one or more of FIGS. 1-9, preferably includes storage device 154 configured to store data associated with the intracranial signals, the extracranial signals, the extracranial oxygen saturation, the intracranial oxygen saturation, and the indication of ICP.

Systems 10, 10', FIGS. 1-9 also preferably includes a power supply coupled to at least one intracranial light source 12, at least one extracranial light source 24, first or intracranial detector 32, second or extracranial detector 122, processing subsystem 40 and/or display 152 e.g., exemplarily shown by power supply 152, FIGS. 1-9.

Figure 10:
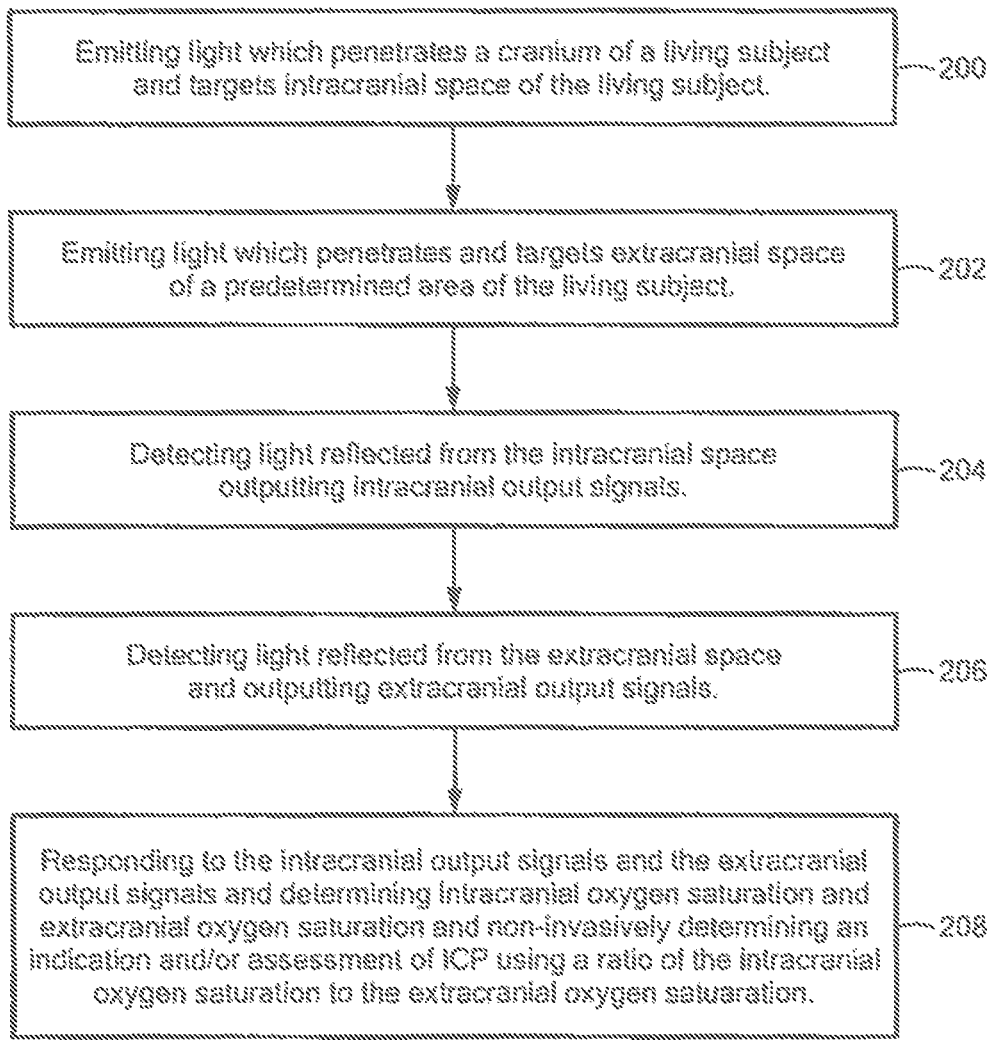
FIG. 10 is a flowchart showing one example of the primary steps of the method for non-invasively determining an indication and/or an assessment of intracranial pressure.

One example of the method for non-invasively determining and/or assessing ICP preferably includes emitting light which penetrates a cranium of a living subject, step 200, FIG. 10, and emitting light which penetrates and targets the extracranial space of a living subject, step 202. The method also includes detecting light reflected from the intracranial space and outputting intracranial output signals, step 204, and detecting light reflected from the extracranial space and outputting extracranial output signals, step 206. The method also includes responding to the intracranial output signals and the extracranial output signals and determining intracranial oxygen saturation and extracranial oxygen saturation and non-invasively determining an indication and/or an assessment of ICP using a ratio of the intracranial oxygen saturation to the extracranial oxygen saturation, step 208.

Preferably, the step of emitting light which penetrates the cranium of the living subject and targets the intracranial space and emitting light which penetrates and targets the extracranial space of the living subject includes emitting light having a wavelength in the range of about 500 nm to about 1,000 nm. Emitting light which penetrates the cranium of the living subject and targets the intracranial space preferably includes emitting light at one or more first predetermined wavelengths and emitting light at one or more second predetermined wavelengths, as discussed above with reference to one or more of FIGS. 1-9. Preferably, emitting light which penetrates and targets the extracranial space of the living subject includes emitting light at one or more first predetermined wavelengths and emitting light at one or more second predetermined wavelengths, as discussed above with reference to one or more of FIGS. 1-9. Preferably, one of live first predetermined wavelengths or live second predetermined wavelengths target oxyhemoglobin chromophores and the other of the first predetermined wavelengths, or second predetermined wavelengths target deoxyhemoglobin chromophores, as discussed above with reference to one or more of FIGS. 1-9.

The result is the arrangement and use of at least one intracranial light source that emits light that penetrates the cranium and targets intracranial space of a living subject, at least one extracranial light source that emits light which penetrates and targets extracranial space of the living subject, a detector subsystem that detects reflected light from the intracranial space and the extracranial space, and a processing subsystem that determines intracranial oxygen saturation and extracranial oxygen saturation non-invasively determines an indication and/or an assessment of ICP using a ratio of the intracranial oxygen saturation to the extracranial oxygen saturation provides an accurate, effective and timely indication and/or assessment of ICP. Thus, system 10 and the method thereof may efficiently, effectively, and timely provide medical care those who may have experienced trauma to the brain. Additionally, system 10 may be more compact, inexpensive, robust, and power efficient system than conventional invasive systems discussed in at least the Background section above.

Although specific features of the invention are shown in some drawings and not in others, this is for convenience only as each feature may be combined with any or all of die other features in accordance with the invention. The words "including", "comprising", "having", and "with" as used herein are to be interpreted broadly and comprehensively and are not limited to any physical interconnection. Moreover, any embodiments disclosed in the subject application are not to be taken as the only possible embodiments.

In addition, any amendment presented during the prosecution of the patent application for this patent is not a disclaimer of any claim element presented in the application as filed: those skilled in the art cannot reasonably be expected to draft a claim that would literally encompass all possible equivalents, many equivalents will be unforeseeable at the time of the amendment and are beyond a fair interpretation of what is to be surrendered (if anything), the rationale underlying the amendment may bear no more than a tangential relation to many equivalents, and/or there are many other reasons the applicant cannot be expected to describe certain insubstantial substitutes for any claim element amended.

Other embodiments will occur to those skilled in the an and are within the following claims.

What is claimed is:

1. A system for non-invasively determining an indication and/or an assessment of intracranial pressure (ICP), the system comprising:
   at least one first light-based sensor and a measuring apparatus that determines intracranial or cerebral oxygen saturation in response to reflected light detected from intracranial space of a living subject;
   at least one second light-based sensor and the measuring apparatus that determines extracranial or extracerebral oxygen saturation in response to reflected light detected from extracranial space of the living subject; and
   a processing subsystem coupled to the at least one first light-based sensor, the measuring apparatus, and the at least one second light-based sensor, the processing subsystem configured to determine the indication and/or the assessment of ICP using a ratio of the intracranial oxygen saturation to the extracranial oxygen saturation.

2. A method for non-invasively determining an indication and/or an assessment of intracranial pressure (ICP), the method comprising:
   determining intracranial or cerebral oxygen saturation in response to reflected light detected from intracranial space of a living subject;
   determining extracranial or extracerebral oxygen saturation in response to reflected light detected from extracranial space of the living subject; and determining the indication and/or the assessment of ICP using a ratio of the intracranial oxygen saturation to the extracranial oxygen saturation.

\* \* \* \* \*